US012658306B2

(12) United States Patent
Braunagel et al.

(10) Patent No.: US 12,658,306 B2
(45) Date of Patent: Jun. 16, 2026

(54) DEVICE AT THE POINT OF IMAGING FOR INTEGRATING TRAINING OF AI ALGORITHMS INTO THE CLINICAL WORKFLOW

(71) Applicant: KONINKLIJKE PHILIPS N.V., Eindhoven (NL)

(72) Inventors: Andre Braunagel, Garching (DE); Karsten Rindt, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 508 days.

(21) Appl. No.: 18/027,947

(22) PCT Filed: Sep. 16, 2021

(86) PCT No.: PCT/EP2021/075484
§ 371 (c)(1),
(2) Date: Mar. 23, 2023

(87) PCT Pub. No.: WO2022/063675
PCT Pub. Date: Mar. 31, 2022

(65) Prior Publication Data
US 2023/0368895 A1       Nov. 16, 2023

(30) Foreign Application Priority Data
Sep. 24, 2020     (EP) ..................................... 20197985

(51) Int. Cl.
*G06K 9/00*          (2022.01)
*G06T 7/00*          (2017.01)
(Continued)

(52) U.S. Cl.
CPC ........... *G16H 30/40* (2018.01); *G06T 7/0002* (2013.01); *G16H 30/20* (2018.01); *G16H 50/20* (2018.01); *G06T 2207/30168* (2013.01)

(58) Field of Classification Search
CPC ........ G16H 30/40; G16H 30/20; G16H 50/20; G16H 50/70; G06T 7/0002; G06T 2207/30168
See application file for complete search history.

(56) References Cited

U.S. PATENT DOCUMENTS

| 11,712,208 | B2 | 8/2023 | Nye |
| 2014/0219548 | A1 | 8/2014 | Wels |

(Continued)

FOREIGN PATENT DOCUMENTS

| CN | 106537396 A | * | 3/2017 | ............. G16H 40/63 |
| WO | WO2017151757 A1 | | 9/2017 | |
| WO | WO2019052810 A1 | | 3/2019 | |

OTHER PUBLICATIONS

PCT International Search Report, International application No. PCT/EP2021/075484, Jan. 7, 2022.

*Primary Examiner* — Xin Jia
(74) *Attorney, Agent, or Firm* — Larry Liberchuk

(57) ABSTRACT

The present invention relates to image processing. In order to facilitate a sustainable infrastructure for training of AI algorithms, an imaging system is proposed with a mobile annotation device to receive an image acquired by the medical imaging apparatus (e.g. x-ray, CT or MRI scanner) in real-time, that is, during the imaging session. The image acquired by the medical imaging apparatus is then displayed, thereby allowing the user to annotate the acquired image. The user annotation may comprise one or more of a recommended workflow in relation to the patient, an indication of an image quality in relation to the first image, an indication on a medical finding, a priority information representing the urgency of the medical finding. The acquired image and the user annotation are then stored in a database, thereby creating a training database for training of (Continued)

the AI algorithm. Alternatively or additionally, the user interface may receive a user annotation in relation to the set of pre-image settings used by the medical imaging apparatus for acquiring the image of the patient. In an example of x-ray chest imaging, the user annotation could be collimation settings, the exposure time settings, the tube voltage settings, the focal spot size settings, the selection of the X-ray sensitive areas for an X-ray imaging system to apply the correct dose to the patient, etc. The set of pre-image settings and the user annotation are then stored in a training database, thereby creating a training database for training of the AI algorithm. In this way, the images and the sets of pre-image settings can be directly chosen from the clinical workflow and there is no need to select the images and/or the sets of pre-image settings and transfer them somewhere else (e.g. from other facilities) for the development. Accordingly, the parameters of the AI algorithm, which has been trained using the training data from the training database, are adapted to fit the needs and standards of a particular facility, which makes it possible to obtain a sustainable architecture that can be used to train AI algorithms for different applications based on the customer's needs.

11 Claims, 6 Drawing Sheets

(51) Int. Cl.

| | |
|---|---|
| *G16H 30/20* | (2018.01) |
| *G16H 30/40* | (2018.01) |
| *G16H 50/20* | (2018.01) |

(56) References Cited

U.S. PATENT DOCUMENTS

| | | | |
|---|---|---|---|
| 2016/0350919 A1 | 12/2016 | Steigauf | |
| 2017/0103532 A1 | 4/2017 | Ghesu | |
| 2020/0104994 A1* | 4/2020 | Sharma | ................ G06T 11/003 |
| 2020/0226757 A1 | 7/2020 | Hare, II | |
| 2022/0301686 A1 | 9/2022 | Rohse | |

* cited by examiner

14

14a

14c

14b

14d user

14

20

DEVICE AT THE POINT OF IMAGING FOR INTEGRATING TRAINING OF AI ALGORITHMS INTO THE CLINICAL WORKFLOW

FIELD OF THE INVENTION

The present invention generally relates to image processing, and in particular to an imaging system, a method of image processing, a computer program element, and a computer readable medium.

BACKGROUND OF THE INVENTION

Previously, it was largely expert operators such as radiographers (x-ray, CT or MRI), sonographers (ultrasound), or nuclear medicine technicians (NM imaging) that operated medical imaging equipment. However, a new trend is emerging wherein less qualified staff is put in charge to perform examinations. This practice, without safeguarding, may lead to a loss of clinical quality.

The operator (referred to herein as "the user") is responsible for performing a set of work-steps throughout the examination, including for example, depending on the modality and the specifics of equipment:

(i) patient positioning (ii) adapt parameters of the imaging scan, (iii) perform acquisition itself, and (iv) review and post-process the resulting images at a console of the imaging equipment.

Once the imaging examination has been completed, subsequent steps in modern radiology workflows are typically organized such that the operator sends the images electronically to an image database (PACS) for storage, and simultaneously via a reading-worklist to another trained expert (medically-certified radiologist), for interpretation of the images. Depending upon a number of factors such as the urgency of the medical situation and the institution-specific organization of the workload, this interpretation often takes place in an asynchronous manner, meaning there is a significant time-delay between image acquisition and the image interpretation.

Artificial intelligence (AI) has the potential to compensate the lack of qualified personnel, while also improving clinical efficiency. AI systems are computer-implemented systems. They are based on machine learning algorithms that have been pre-trained on training data to perform a task, such as assisting the user during the examination. For training the machine learning algorithms, the training data has to be prepared for the development of the AI algorithm, which implies a high effort in the development process. Additionally, AI algorithms that have been trained in a different facility may not always fit the needs and the standards of a different facility, which makes it very difficult to obtain a sustainable architecture that can be used to train AI algorithms for different applications based on customer needs.

SUMMARY OF THE INVENTION

There may be a need to for systems and methods to address at least some of the above noted deficiencies.

The object of the present invention is solved by the subject-matter of the independent claims, wherein further embodiments are incorporated in the dependent claims. It should be noted that the following described aspects of the invention apply also for the imaging system, the method of image processing, the computer program element, and the computer readable medium.

According to a first aspect of the present invention, there is provided an imaging system, comprising:

a medical imaging apparatus configured to use a set of pre-image settings for acquiring an image of a patient in an imaging session;

a user interface configured to receive a user annotation in relation to (i) the acquired image of the patient and/or (ii) the set of pre-image settings used by the medical imaging apparatus for acquiring the image of the patient;

at least one training database configured to store (i) the acquired image of the patient and the received user annotation and/or (ii) the set of pre-image settings and the received user annotation; and a training module configured to train at least one data-driven model with training data obtained from the at least one training database.

AI has shown high potential to enhance the clinical workflow. Therefore, there are many attempts to develop AI algorithms that can be used in the clinical workflow. However, training of these algorithms is very challenging, as it requires well-annotated clinical data. Typically, this implies that a big effort has to be spent to find the suitable data and to annotate it.

In order to facilitate a sustainable infrastructure for training of AI algorithms, an imaging system is proposed that comprises a medical imaging system (e.g. x-ray, CT or MRI scanner) for acquiring an image of a patient. The image acquired by the medical imaging apparatus is then displayed and the user has the possibility to annotate the image via a user interface.

In an example, the user interface may receive a user annotation in relation to an image of the patient acquired by a medical imaging apparatus (e.g. x-ray, CT or MRI scanner). Examples of the user annotation may include, but are not limited to, an indication of image quality and a clinical finding. The user interface may be configured to receive the acquired image of the patient in real-time, e.g. right after image acquisition at the imaging system. The acquired image and the user annotation are then stored in a training database, thereby creating a training database for training of the AI algorithm.

Alternatively or additionally, the user interface may receive a user annotation in relation to the set of pre-image settings used by the medical imaging apparatus for acquiring the image of the patient. In an example of x-ray chest imaging, the user annotation could be collimation settings, the exposure time settings, the tube voltage settings, the focal spot size settings, the selection of the X-ray sensitive areas for an X-ray imaging system to apply the correct dose to the patient, etc. The set of pre-image settings and the user annotation are then stored in a training database, thereby creating a training database for training of the AI algorithm.

In this way, the images and the sets of pre-image settings can be directly chosen from the clinical workflow and there is no need to select the images and/or the sets of pre-image settings and transfer them somewhere else (e.g. from other facilities) for the development. Accordingly, the parameters of the AI algorithm, which has been trained using the training data from the training database, are adapted to fit the needs and standards of a particular facility, which makes it possible to obtain a sustainable architecture that can be used to train AI algorithms for different applications based on the customer's needs.

In an example, the training module may be implemented in a processor circuitry configured for parallel computing, for instance a multicore processor, a GPU or parts thereof. In another example, the training module may be included in a system-on-chip (SoC) circuitry.

In an example, the user interface may be part of a handheld device including one or more of: a mobile phone, a laptop computing device, and a tablet computer.

In another example, the user interface may be part of the medical imaging apparatus.

In an example, the medical imaging apparatus, the training module, and the user interface may have a wired connection (e.g. USB, coaxial or optical cable, etc.) and/or wireless connection (e.g. Bluetooth, NFC, WLAN, etc.).

In an example, a network may communicatively couple the medical imaging apparatus, the training module, and the user interface. The network may be the internet. The network may alternatively be any other type and number of networks. For example, the network may be implemented by several local area networks connected to a wide area network. For example, the network may comprise any combination of wired networks, wireless networks, wide area networks, local area networks, etc.

According to an embodiment of the present invention, wherein the at least one data-driven model comprises one or more of:

a data-driven model to analyze the acquired image of the patient to compute medical decision support information; and a data-driven model to analyze a camera image of the patient to compute a set of pre-image settings, wherein the camera image is generated on the basis of sensor data obtained from a sensor arrangement, which has a field of view including at least part of an area, where the patient is positioned for imaging.

The medical decision support information may comprise e.g. a recommended workflow in relation to the patient, an indication of an image quality in relation to the acquired image, an indication on a medical finding, and a priority information representing urgency of a medical finding.

The camera image may be in the form of a depth image or an RGB image. The camera image may be acquired when the patient is positioned for the imaging examination, e.g., by lying or standing with the field of view of the imaging system. The camera image does not necessarily have to include the whole body surface of the patient; it may relate to only part of the body surface of the patient, which is relevant for the imaging examination. For example, if an anatomy of interest is a neck of the patient, only the measurement image of the upper body of the patient may be captured by the sensor arrangement.

According to an embodiment of the present invention, the medical imaging apparatus comprises the user interface.

For example, the medical imaging apparatus may comprise a touch screen that allows the user to input the user annotation.

According to an embodiment of the present invention, the imaging system further comprises a mobile annotation device that comprises:

an input channel configured to receive (i) the acquired image of the patient and/or (ii) the set of pre-image settings used by the medical imaging apparatus for acquiring the image of the patient;

a display configured to display (i) the acquired image of the patient and/or (ii) the set of pre-image settings used by the medical imaging apparatus for acquiring the image of the patient;

the user interface configured to receive a user annotation in relation to (i) the acquired image of the patient and/or (ii) the set of pre-image settings used by the medical imaging apparatus for acquiring the image of the patient; and an output channel configured to provide (i) the acquired image of the patient and the received user annotation and/or (ii) the set of pre-image settings and the received user annotation to the at least one training database.

For example, the mobile annotation device is a handheld device including one or more of: a mobile phone, a laptop computing device, and a tablet computer.

The mobile annotation device may be placed close to the radiologist's reading monitor as shown in FIG. 4. Each time that a radiologists opens an image, the image may be additionally displayed on the mobile annotation device 14. On the mobile annotation device, the radiologist has the possibility to annotate the image with respect to e.g. image quality, clinical findings, etc.

According to an embodiment of the present invention, the training module is configured to repeatedly train the at least one data-driven model.

In an example, the data-driven model may be trained on the fly on a new instance of images acquired by the medical imaging apparatus. In other words, the training mode may be continued in repeated training phases in the deployment phase. For example, the training module of the image-processing device may be configured to train the data-driven model on the fly (i.e. during normal use of the data-driven model in the deployment phase) on the acquired image of the patient and the user annotation provided by the mobile annotation device. For example, each newly acquired image and the respective user annotation provided by the mobile annotation device may be directly sent to the training module for updating the parameters of the data-driven model. In this way, the data-driven model is continuously trained, such that the data-driven model fits the needs and standards of a particular facility.

In another example, the data-driven model is not trained on the fly, but after a certain number of images with annotation have been collected.

In a further example, once the user does not agree with the feedback of the algorithm displayed on the mobile device, he/she may choose a new annotation for the image. The database is then enriched not only by this image but by all possible variations of the image (such as the same image but slightly cut-off). This data enrichment step may allow to increase the weight of this image that was wrongly annotated by the algorithm, as the algorithm is then retrained using the new image and all the newly generated image variations.

According to an embodiment of the present invention, the training module is configured to generate a user annotation on a random basis for starting training the data-driven model.

In other words, the initial model is a naïve model—that is to say that the first image feedback is generated on a random basis. This means that the model can be trained from scratch.

According to an embodiment of the present invention, the data-driven model is configured to provide a suggestion based on the computed medical decision support information for allowing a user to actively accept or reject the provided suggestion.

In other words, a further possibility is that the model provides only a suggestion and the user needs to actively accept or reject the suggestion, as opposed to the possibility where the output user input can be a number of predefined tags (e.g. different diseases).

According to an embodiment of the present invention, the medical imaging system comprises:

a first group of medical imaging apparatuses and a second group of medical imaging apparatuses, which is different from the first group of medical imaging apparatuses;

wherein the user interface is configured to receive:

a first user annotation in relation to (i) an image of a patient acquired by a medical imaging apparatus in the first group and/or (ii) a set of pre-image settings used by a medical imaging apparatus in the first group; and a second user annotation in relation to (i) an image of a patient acquired by a medical imaging apparatus in the second group and/or (ii) a set of pre-image settings used by a medical imaging apparatus in the second group;

wherein the at least one training database (16) comprises:

a first training database for storing (i) the image of a patient acquired by a medical imaging apparatus in the first group and the received user annotation and/or (ii) the set of pre-image settings used by a medical imaging apparatus in the first group and the received user annotation; and a second training database for (i) the image of a patient acquired by a medical imaging apparatus in the second group and the received user annotation and/or (ii) the set of pre-image settings used by a medical imaging apparatus in the second group and the received user annotation;

wherein the training module is configured to train a first data-driven model with training data obtained from the first training database and to train a second data-driven model with training data obtained from the second training database.

In this way, the images and/or pre-image settings for training purposes are directly taken from the clinical workflow, the training can be performed according to the standards of each group (e.g. user group, or facility). The proposed IT infrastructure may offer a method to integrate training of AI algorithms into the clinical workflow and to make the training group-specific.

According to an embodiment of the present invention, the first group of medical imaging apparatuses and the second group of medical imaging apparatuses are from different facilities and/or different user groups.

According to an embodiment of the present invention, the user annotation comprises one or more of:

an indication of image quality;

a clinical finding; and an indication of a set of desired pre-image settings.

In an example, the indication on image quality includes an indication of one any one or more of a) patient positioning, b) collimator setting, c) contrast, d) resolution, e) noise, and f) artifact.

The term "clinical finding" may also be referred to as medical finding.

In an example, the indication of a set of desired pre-image settings e.g. for CT may include collimation settings, the exposure time settings, the tube voltage settings, the focal spot size settings, and/or the selection of the X-ray sensitive areas for an X-ray imaging system.

According to an embodiment of the present invention, the decision support information includes one or more of:

a recommended workflow in relation to the patient;

an indication of an image quality in relation to the acquired image;

an indication on a medical finding; and a priority information representing urgency of a medical finding.

For example, the recommend workflow may be in variance to a previously defined workflow envisaged for the said patient.

According to an embodiment of the present invention, the mobile annotation device is a handheld device including one or more of: a mobile phone, a laptop computing device, and a tablet computer.

According to a second aspect of the present invention, there is provided a method of image processing, comprising:

acquiring, by a medical imaging apparatus using a set of pre-image settings, an image of a patient in an imaging session;

receiving, via a user interface, a user annotation in relation to (i) the acquired image of the patient and/or (ii) the set of pre-image settings used by the medical imaging apparatus for acquiring the image of the patient;

storing, in at least one training database, (i) the acquired image of the patient and the received user annotation and/or (ii) the set of pre-image settings and the received user annotation; and training, by a training module, at least one data-driven model with training data obtained from the at least one training database.

According to another aspect of the present invention, there is provided a computer program element configured, which, when being executed by at least one processing unit, is adapted to cause the imaging system according to the first aspect and any associated example to perform the method according to the second aspect and any associated example.

According to a further aspect of the present invention, there is provided a computer readable medium comprising the computer program element.

Advantageously, the benefits provided by any of the above aspects equally apply to all of the other aspects and vice versa.

As used herein, the term "user" refers to medical personnel at least partly involved in an administrative or organizational manner in the imaging procedure.

As used herein, the term "patient" refers to a person, or in veterinary settings, an animal (in particular a mammal), who is being imaged.

As used herein, the term "machine-learning" refers to the field of the computer sciences that studies the design of computer programs able to induce patterns, regularities, or rules from past experiences to develop an appropriate response to future data, or describe the data in some meaningful way.

As used herein, the term "learning" in the context of machine learning refers to the identification and training of suitable algorithms to accomplish tasks of interest. The learning, that is, the performance of the machine learning of a task measurable by a performance metric, generally improves with the training data.

As used herein, the term "data-driven model" in the context of machine learning refers to a suitable algorithm that is trained on the basis of appropriate training data. As will be explained hereafter, a neural-network model is shown as may be used in examples. However, other machine learning techniques such as support vector machines, decision trees or other may be used instead of neural networks. An exemplary data-driven model is illustrated in FIG. 8.

As used herein, the term "module" may refer to, be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

In the following, the approach is described in detail in relation with a data-driven model for analyzing the acquired image of the patient to compute medical decision support information. Although the following detailed description is described with respect to a particular data-driven model for the purposes of illustration, anyone of ordinary skill in the art will appreciate that the method, and imaging system described above and below can be adapted to any other data-driven model, such as a data-driven model to analyze a camera image of the patient to compute the set of pre-image settings. Accordingly, the following described examples are set forth without any loss of generality to, and without imposing limitations upon, the claimed invention.

Figure 1:
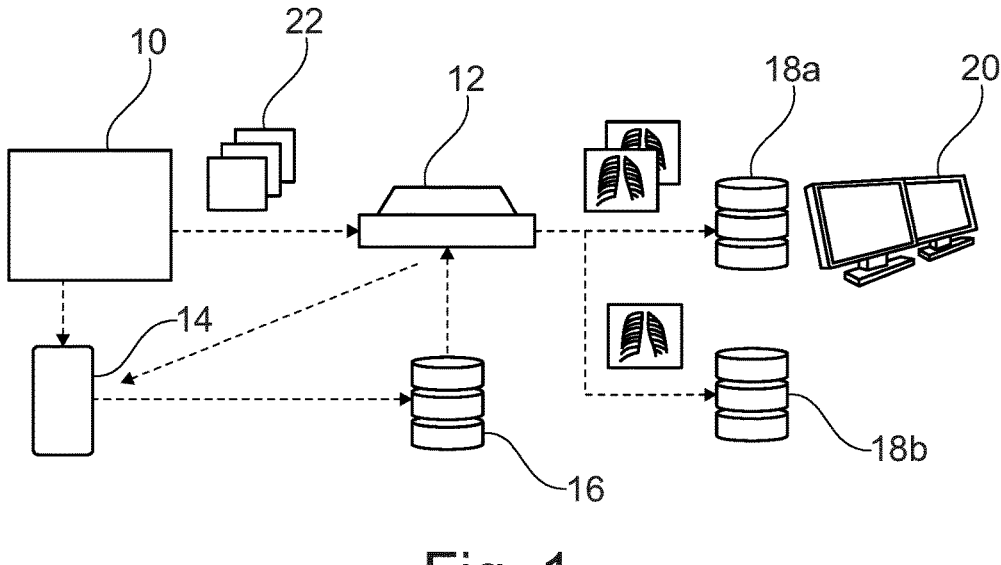
FIG. 1 shows a schematic block diagram of an exemplary medical imaging system.

FIG. 1 shows a schematic block diagram of an exemplary medical imaging system 100. The medical imaging system 100 comprises a medical imaging apparatus 10, an image-processing device 12, a mobile annotation device 14, a training database 16, an image database 18a, 18b, and a display arrangement 20.

The medical imaging apparatus 10 is configured for acquiring an image 22 of a patient in an imaging session. The medical imaging apparatus 10 may be of any modality such as transmission or emission imaging. Transmission imaging includes for instance x-ray based imaging carried out with a CT scanner or other. Magnetic resonance imaging MRI is also envisaged and so is ultrasound imaging. Emission imaging includes PET/SPECT and other nuclear medicine modalities. During an imaging session, images 22 are acquired of the patient. The images 20 are preferably in digital form and may assist a physician in diagnosis.

The image-processing device 12 comprises an image analyzer 26 configured to apply a data-driven model to analyze the acquired image of the patient to compute medical decision support information. In an example, the image-processing device 14 is a mobile device, such as, but not limited to, a mobile phone, a laptop computing device, or a tablet computer. In another example, the image-processing device 12 is a server that provides the computing service. In a further example, the imaging processing device 12 is a workstation with the display arrangement 18.

Figure 2:
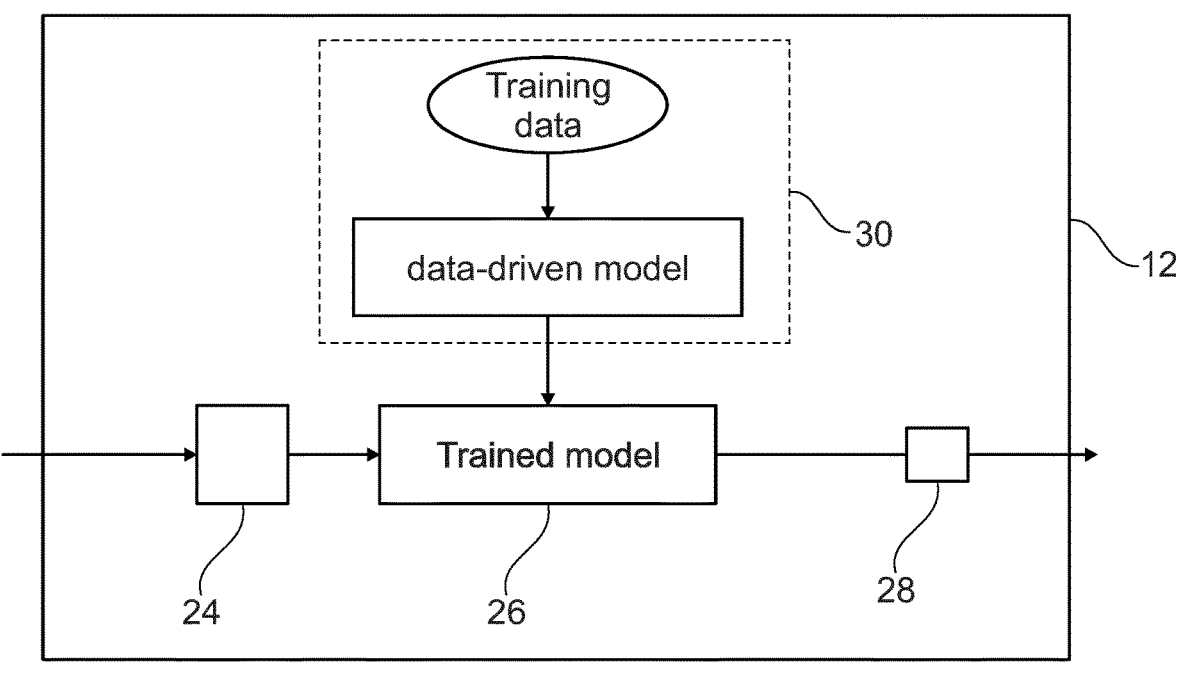
FIG. 2 shows a schematic block diagram of an exemplary imaging processing device.

FIG. 2 shows a schematic block diagram of an exemplary image-processing device 12. In this example, the image-processing device 12 comprises an input channel 24, an image analyzer 26, and an output channel 28.

The input channel 24 may be configured to receive the acquired image 22 of a patient in an imaging session. The input channel 12 may be, in an example, implemented as an Ethernet interface, a USB™ interface, a wireless interface such as a Wi-Fi™ or Bluetooth™ or any comparable data transfer interface enabling data transfer between input peripherals and the image analyzer 26. Furthermore, the input channel may access data over a network, such as the internet or any combination of wired networks, wireless networks, wide area networks, local area networks, etc.

The image analyzer 26 of the image-processing device 12 may be driven by artificial intelligence. In particular, the image analyzer 26 may be included as a pre-trained data-driven model. The image analyzer may be run on a processing unit of image-processing device 12. The processing unit may include general purpose circuitry and/or dedicated computing circuitry such as a GPU or may be a dedicated core of a multi-core multi-processor. Preferably, the processing unit is configured for parallel computing. This is in particular advantageous if the underlying machine-learning model is a neural network such as a convolutional network. Such types of machine learning models can be efficiently implemented by vector, matrix or tensor multiplications. Such types of computations can be accelerated in a parallel computing infrastructure.

The decision support information computed by the image analyzer 26 may hence include any one or more of the following: image quality, medical finding and/or in associated priority level. The image quality analysis may include an assessment of patient positioning, collimator setting (if any), contrast, resolution, image noise or artifacts. Some or all of these factors may be considered and represented as a single image quality score in a suitable metric or each factor is measured by a separate score in a different metric.

If the image quality of an image is found by the decision support information to be acceptable, the image may be sent to a different image database 18a.

If the image quality of an image is found by the decision support information to be deficient, image may be sent to the image database 18b. Additionally, a suggestive graphical indication may be given when the image quality is deemed optimal. For instance, a suggestive "tick" symbol may be displayed in an apt coloring scheme, such as green or otherwise. If the image quality is found to be inadequate, this is also indicated on the onboard display in suggestive symbology such as a red cross or otherwise.

If a medical condition is found, this is indicated by a suitable textual or other symbol on the onboard display of the mobile display device. In addition, or instead, if a medical condition is found, a related workflow may be suggested. This suggested workflow may be different from the currently assigned plan. Additionally, a retake may be proposed, optionally with a suggestion for updated imaging parameters. The user may then accept the retake using the user interface, and a suitably formatted message is sent to the operating console to adjust the imaging parameters and/or initiate the image retake.

Preferably the computing of the decision support information is done in a two-stage sequential processing flow. In a first stage, the image quality is established. If the image quality is found to be sufficient, only then is the imagery analyzed for a medical finding and/or workflow suggestions. The workflow computed based on the analyzed image may differ from a workflow originally associated with the patient at check-in for instance. This change in workflow may be required for instance if an unexpected medical condition is detected in the image that was not previously envisaged by the original workflow. For instance, if the patient is to receive a cancer treatment of a certain organ, such as the liver, a certain workflow is envisaged. However, if the analysis of the copy image accidentally reveals that the patient is in fact suffering from pneumonia, the workflow needs to be changed to first treat pneumonia before proceeding with the cancer treatment.

The image-processing device 12 may further comprise a training module 30 for training the data-driven module. In order to train the data-driven module, training data is collected from the training database 16.

The output channel 28 is configured to provide the decision support information, e.g. to a display arrangement 20 (for example, a built-in screen, a connected monitor or projector) or to a file storage (for example, a hard drive or a solid state drive), such as image database 18a, 18b.

Figure 3:
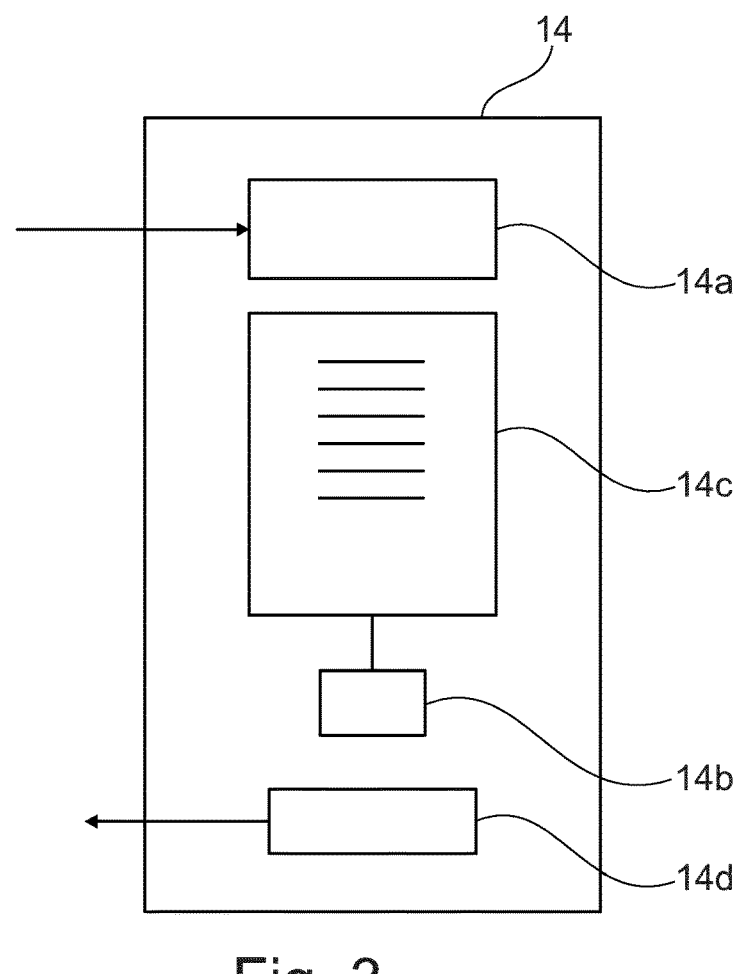
FIG. 3 shows a schematic block diagram of an exemplary mobile annotation device.

FIG. 3 shows a schematic block diagram of an exemplary mobile annotation device 14. The mobile annotation device 14 may include any type of wireless device such as consumer electronics devices, smart phones, tablet personal computers, wearable computing devices, personal digital assistants (PDAs), laptop computers, and/or any other like physical computing device.

In the example of FIG. 3, a single mobile annotation device 14 is illustrated. However, it will be appreciated there may be a plurality of mobile annotation devices 14 to receive a plurality of user annotations from different users and to provide the acquired image of the patient together with the plurality of user annotations to the training database for training the data-driven model. In other words, two or more users may have the possibility to add their user annotations to the training database. This may provide comprehensive annotations of the acquired image and minimize opinion bias. In this way, the quality of the training data may be improved.

The mobile annotation device 14 comprises an input channel 14a, a display 14b, a user interface 14c, and an output channel 14d.

The input channel 14a is configured to receive the acquired image of the patient. The input channel 14a may be a universal interface and affords interoperability with a range of different medical imaging apparatuses, even of different modalities. In an example, the input channel 14a is configured to receive the acquired image based on direct imaging ("image of-image") of the displayed image. In other examples, the input channel 14a is arranged as NFC or Bluetooth, if imaging apparatus is so equipped. Other examples still include LAN, WLAN, etc.

The display 14b is configured to display the acquired image of the patient. As the acquired image is displayed on the mobile annotation device 14, the user has the possibility to annotate the image.

The user interface 14c is configured to receive a user annotation in relation to the acquired image of the patient. The term "user interface" may refer to an interface between a human user or operator and one or more devices that enables communication between the user and the device(s). Further examples of user interfaces that may be employed in various implementations of the present disclosure include, but are not limited to, switches, potentiometers, buttons, dials, sliders, track balls, display screens, various types of graphical user interfaces (GUIs), touch screens, microphones, and other types of sensors that may receive some form of human-generated stimulus and generate a signal in response thereto.

In an example, the use may have the possibility to annotate the image with predefined parameters, e.g. predefined tags (e.g. for different diseases). In an example, the user may use the mobile annotation device 14, e.g. a client, such as a web-based thin client, to access the tailored content for annotating the image. The mobile annotation device 14 may be used with the thin-client as an app to access the content for annotating the image. The content may be stored on a database. The content may be customizable, e.g. by an administrator. For example, the content for annotating the image may comprise a list of image qualities to be selected, such as "optimal", "suboptimal", and "bad", a list of clinical findings in relation to a particular disease e.g. in patients with chronic complex regional pain syndrome, etc.

How the "annotation" could look like is discussed on the example of image quality for knee imaging. Each time, the user thinks that the image is good, he/she may choose the option "optimal" on the mobile annotation device 14. In case the image quality/patient positioning is not optimal, the user may choose "suboptimal" on the mobile annotation device 14. Then the input is added to the training database 16 for the data-driven model. Alternatively or additionally, the user annotation may comprise a clinical finding. For example, if a radiologist sees a pneumothorax on the image, he may choose "pneumothorax" on the mobile annotation device 14 and the image may be automatically added to the corresponding training database 16 for the data-driven model. This workflow may have the advantage that the radiologist can choose which images he or she wants to add—i.e. he can exclude the images where he or she is not sure about the findings.

In another example, the data-driven model may provide only a suggestion and the user may need to actively accept or reject the suggestion, as opposed to the possibility where the output user input can be a number of predefined tags (e.g. for different diseases).

Figure 4:
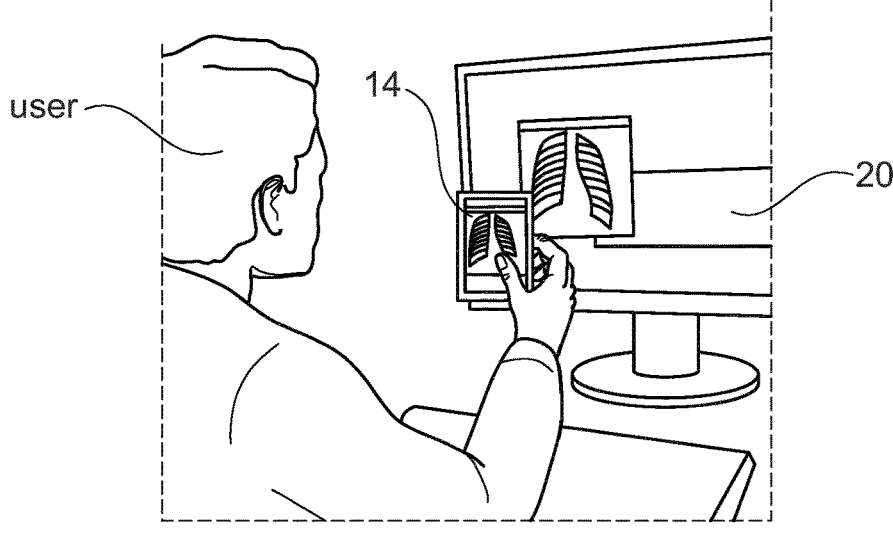
FIG. 4 shows an example of implementing the mobile annotation device for a radiologist.

In order to implement this tool for e.g. the radiologist, the mobile annotation device 14 may be placed close to the radiologist's reading monitor 18 as shown in FIG. 4. Each time that a radiologists opens an image, the image may be additionally displayed on the mobile annotation device 14. On the mobile annotation device 14, the radiologist has the possibility to annotate the image with respect to e.g. image quality, clinical findings, etc.

Turning back to FIG. 3, the output channel 14d is configured to provide the acquired image of the patient and the user annotation to the training database 16 for training the data-driven model.

Once sufficient annotated images have been collected in this manner, the data-driven model may be used to automatically evaluate e.g. the image quality of a newly acquired image and/or clinical findings.

As the images for training purposes are directly taken from the clinical workflow, the training can be performed according to the standards of the institution. Which persons are experienced enough to annotate the data, it can be determined by the institution which person is experienced enough for annotating the data. The proposed IT infrastructure may offer a method to integrate training of AI algorithms into the clinical workflow and to make the training user-specific.

Turning to FIG. 2, the training module 30 may be configured to train the data-driven model using the following steps of receiving the training data, and applying the data-driven model to the training data in one or more iterations. As a result of this application the pre-trained model is then obtained which can then be used in deployment. In deployment, new data, e.g. a new image not from the training set, can be applied to the pre-trained model to obtain the desired decision support information for this new data.

The data-driven model is operable in two modes: "training mode/phase" and "deployment mode/phase". In training mode, an initial model of the data-driven model is trained based on a set of training data to produce a trained data-driven model. In deployment mode, the pre-trained data-driven model is fed with non-training, newly acquired image data, to operate during normal use.

In a further example, the data-driven model is operable in a hybrid mode, where the system is running in an already trained manner, however, if a user sees an image where he/she disagrees with the feedback he can "overrule" the system. For example, as illustrated in FIG. 1, the mobile annotation device 14 may receive and display the medical decision support information computed by the image-processing device 12. If the user disagrees with the computed medical decision support information, the user may provide his/her feedback to overrule the system.

The initial model of the data-driven model may be a naïve model—that is to say that the first image feedback is generated on a random basis. In other words, the training module may be configured to generate a user annotation on a random basis for starting training the data-driven model and the data-driven model may be trained from scratch.

Preferably, the training mode may be continued in repeated training phases in the deployment phase.

In an example, the training module 30 of the image-processing device 12 may be configured to train the data-driven model on the fly (i.e. during normal use of the data-driven model) on each newly acquired image of the patient and the user annotation provided by the mobile annotation device 14. For example, each newly acquired image and the respective user annotation provided by the mobile annotation device 14 may be directly sent to the training module for updating the parameters of the data-driven model. In this way, the data-driven model is continuously trained, such that the parameters of the data-driven model is continuously adapted for fitting the needs and standards of a particular facility.

In another example, the data-driven model is not trained on the fly, but after a certain number of images with annotation have been collected.

Figure 5:
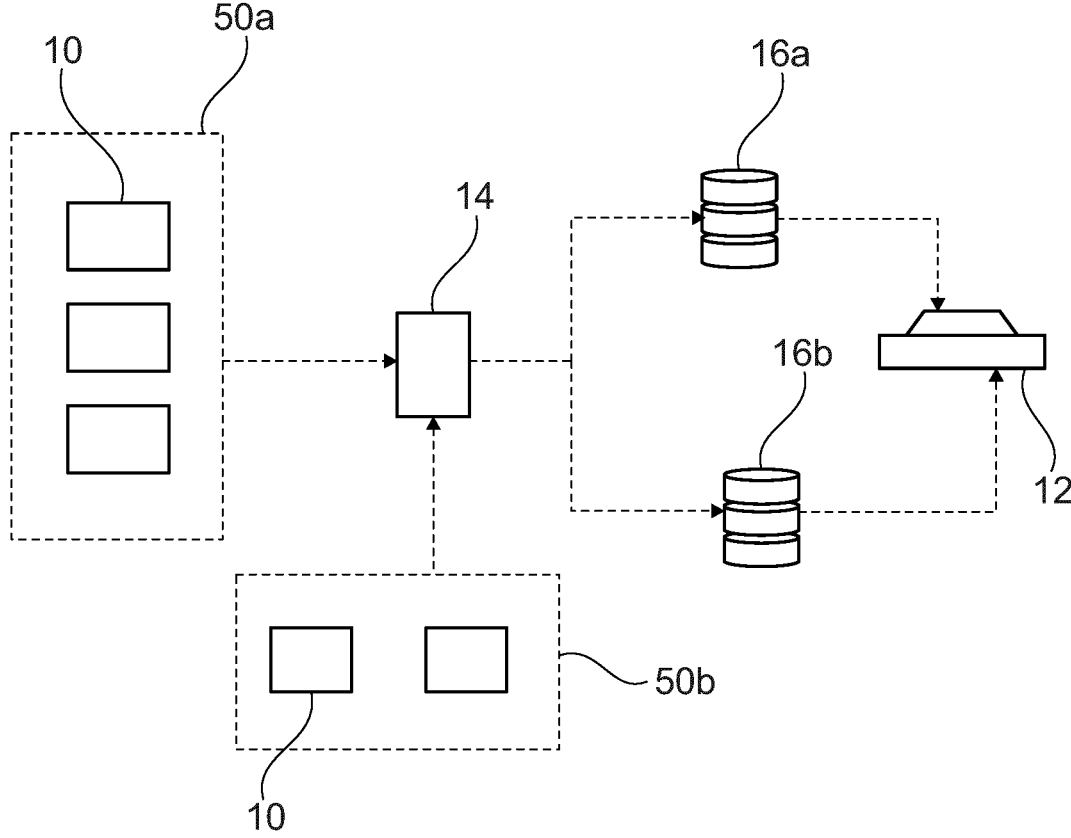
FIG. 5 shows a schematic block diagram of a further exemplary medical imaging system.

FIG. 5 shows a further example of the medical imaging system 100. In this example, the medical imaging system 100 comprises a first group 50a of medical imaging apparatuses and a second group 50b of medical imaging apparatuses, which is different from the first group 50a of medical imaging apparatuses.

In an example, the first and second groups of medical imaging apparatuses may represent different facilities.

In an example, the first and second groups of medical imaging apparatus may represent different user groups.

Each group may comprise one or more medical imaging apparatuses. In the example illustrated in FIG. 5, the first group 50a of medical imaging apparatuses comprises three medical imaging apparatuses, while the second group 50b of medical imaging apparatuses comprises two medical imaging apparatuses.

The image analyzer 26 of the image-processing device 12 is configured to apply a first data-driven model to analyze an image acquired by the first group of medical imaging apparatuses and to apply a second data-driven model to analyze an image acquired by the second group of medical imaging apparatuses.

Figure 6:
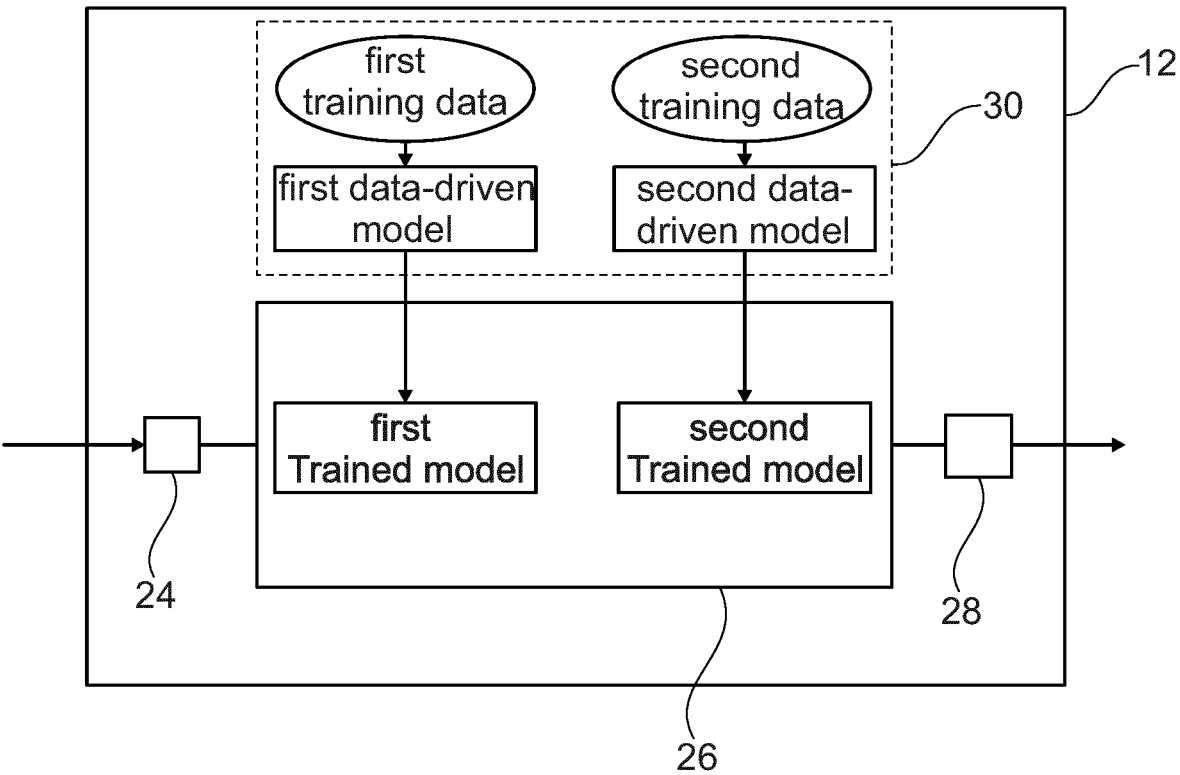
FIG. 6 shows a schematic block diagram of a further exemplary imaging-processing device.

FIG. 6 shows a schematic block diagram of an exemplary imaging processing device 12. The image analyzer 26 is configured to apply a first data-driven model to analyze an image acquired by the first group 50a of medical imaging apparatuses. The image analyzer 26 is configured to apply a second data-driven model to analyze an image acquired by the second group 50b of medical imaging apparatuses.

In an example, the first and second data-driven models may use the same neural networks, e.g. CNN.

In another example, the first and second data-driven models may use different neural networks, such as CNN and recurrent NNs.

In a further example, the first data-driven model may use neural networks and the second data-driven model may use other machine learning techniques such as support vector machines, decision trees, etc.

Turning to FIG. 5, the training data for the first group 50a of medical imaging apparatuses and the second group 50b of medical imaging apparatuses is collected differently. In particular, the mobile annotation device 14 is configured to provide the image acquired by the first group 50a of medical imaging apparatuses together with the user annotation to a first training database 16a for training the first data-driven model. The mobile image annotation apparatus 14 is configured to provide the image acquired by the second group 50b of medical imaging apparatuses together with the user annotation to a second training database 16b for training the second data-driven model. The second training database 16b is different from the first training database 16a.

In an example, the metadata of each acquired image may comprise a group identifier. The mobile annotation device 14 may send the acquired image and user annotation to the corresponding training database 16a, 6b according to the group identifier.

In another example, the metadata of each acquired image may comprise an identifier for the medical imaging apparatus. The mobile annotation device 14 may check a lookup table using the identifier for the medical imaging apparatus to find the corresponding training database 16a, 16b.

In this way, the images for training purposes are directly taken from the clinical workflow of each group, the training can be performed according to the standards of each group (e.g. user group, or facility). The proposed IT infrastructure may offer a method to integrate training of AI algorithms into the clinical workflow and to make the training group-specific.

The exemplary imaging system in FIGS. 1-6 illustrates a user interface in a mobile annotation device 14. Alternatively or additionally (not shown), the user interface may be part of the mobile imaging system. For example, the medical imaging apparatus (e.g. x-ray, MRI, CT, etc.) may comprises a display with a touch screen configured to receive the user annotation.

Figure 7:
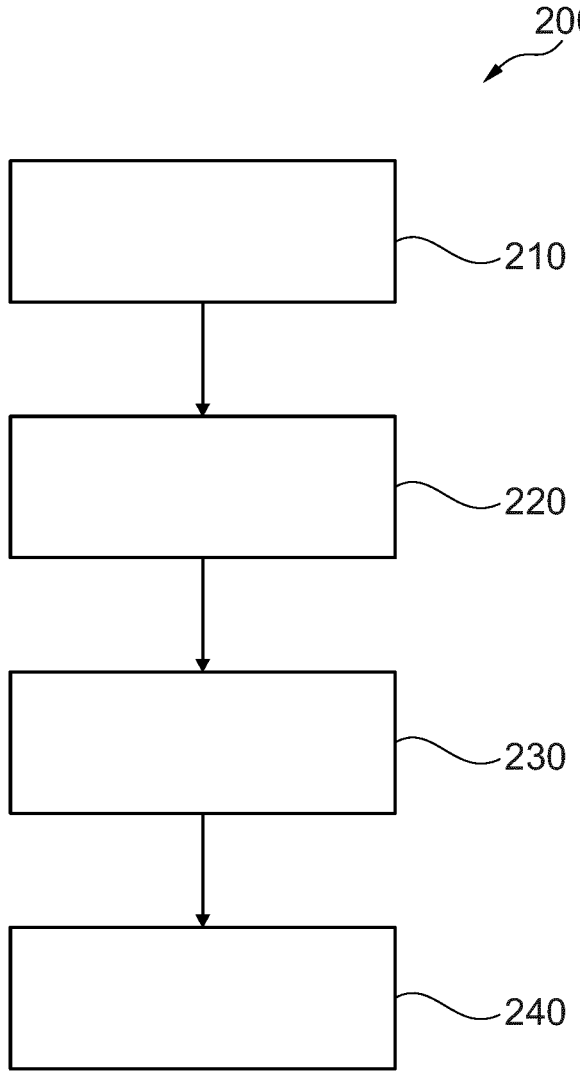
FIG. 7 shows a flow chart of an exemplary method of image processing.

Reference is now made to FIG. 7, which shows a flow chart of a method of image processing that relates to the system described above. However, it will be appreciated that the below described method is not necessarily tied to the above described system the following method may hence be understood as a teaching in its own right.

In step 210, a medical imaging apparatus acquires an image of a patient in an imaging session.

In step 220, a user interface receives a user annotation in relation to the acquired image of the patient. Alternatively or additionally, the user interface receives the set of pre-image settings used by the medical imaging apparatus for acquiring the image of the patient.

In step 230, the acquired image of the patient and the received user annotation are stored in at least one training database. In an example, the user annotation may comprise an indication of image quality. In an example, the user annotation may comprise a clinical finding.

Alternatively or additionally, the set of pre-image settings and the received user annotation are stored in at least one training database.

In step 240, a training module trains at least one data-driven model with training data obtained from the at least one training database.

In an example, an initial model of a data-driven model is trained based on a set of training data to produce a trained data-driven model in a training mode. In deployment mode, the pre-trained data-driven model is fed with non-training, newly acquired image data, to operate during normal use.

In another example, the data-driven model is operable in a hybrid mode, where the system is running in an already trained manner, however, if a user sees an image where he/she disagrees with the feedback he can "overrule" the system. For example, as illustrated in FIG. 1, the mobile annotation device 14 may receive and display the medical decision support information computed by the image-processing device 12. If the user disagrees with the computed medical decision support information, the user may provide his/her feedback to overrule the system.

Optionally, there are a first group of medical imaging apparatuses and a second group of medical imaging apparatuses, which is different from the first group of medical imaging apparatuses. Each group may comprise one or more medical imaging apparatuses. The first group of medical imaging apparatuses and the second group of medical imaging apparatuses may be from different facilities and/or different user groups.

The method 200 may further comprises the step of providing, by the mobile annotation device, the image acquired by the first group of medical imaging apparatuses together with the user annotation to a first training database for training the first data-driven model for analyzing an image acquired by the first group of medical imaging apparatuses.

The method 200 may further comprise the step of providing, by the mobile annotation device, the image acquired by the second group of medical imaging apparatuses and the user annotation to a second training database for training the first data-driven model for analyzing an image acquired by the first group of medical imaging apparatuses. The second training database is different from the first training database.

In this way, the images for training purposes are directly taken from the clinical workflow, the training can be performed according to the standards of each group (e.g. user group, or facility). The proposed IT infrastructure may offer a method to integrate training of AI algorithms into the clinical workflow and to make the training group-specific.

It should also be understood that, unless clearly indicated to the contrary, in any methods claimed herein that include more than one step or act, the order of the steps or acts of the method is not necessarily limited to the order in which the steps or acts of the method are recited.

Figure 8:
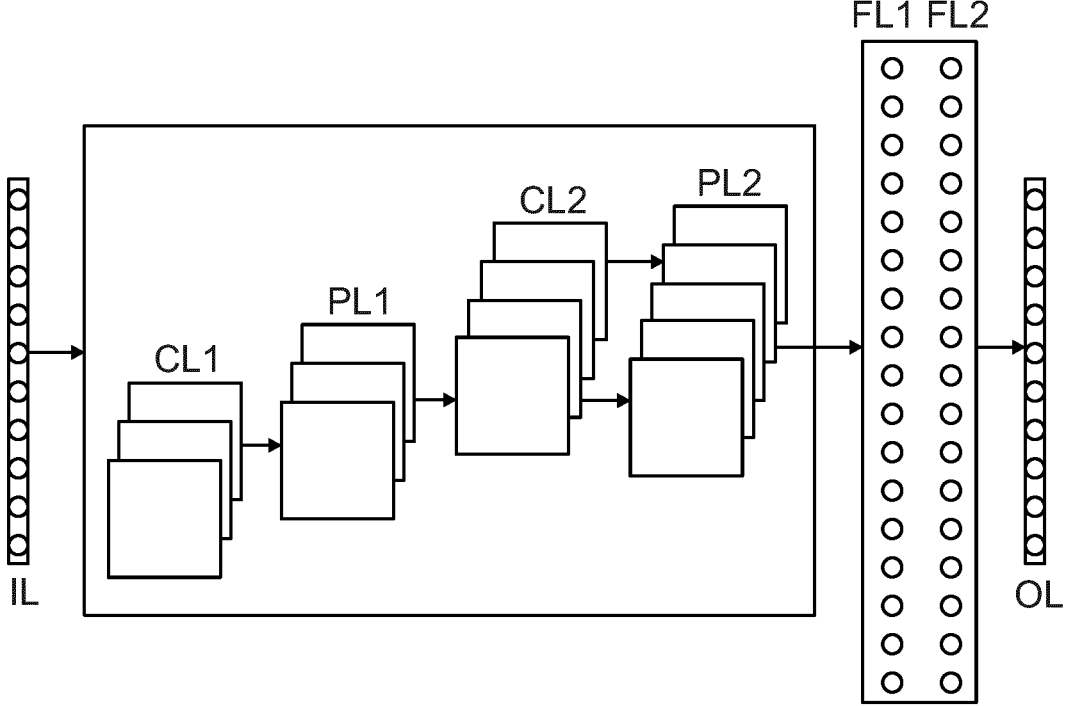
FIG. 8 shows a schematic diagram of an exemplary data-driven model.

Reference is now made to FIG. 8, where a neural-network model is shown as an exemplary data-driven model. However, other machine learning techniques such as support vector machines, decision trees or other may be used instead of neural networks. Having said that, neural networks, in particular convolutional networks, have been found to be of particular benefit especially in relation to image data.

Specifically, FIG. 8 is a schematic diagram of a convolutional neural-network (CNN). A fully configured NN as obtained after training (to be described more fully below) may be thought as representation of an approximation of a latent mapping between two spaces, the images and the space of any one or more of image quality metrics, medical findings and treatment plans. These spaces can be represented as points in a potentially high dimensional space, such as an image being a matrix of N×N, with N being the number of pixels. The image quality metrics, the medical findings and treatment plane may be similarly encoded as vectors, matrices or tensors. For example, a workflow may be implemented as a matrix or vector structure, with each entry representing a workflow step. The learning task may be one or more of classification and/or regression. The input space of images may include 4D matrices to represent a time series of matrices, and hence a video sequence.

A suitable trained machine-learning model or component attempts to approximate this mapping. The approximation may be achieved in a learning or training process where parameters, itself forming a high dimensional space, are adjusted in an optimization scheme based on training data.

In yet more detail, the machine-learning component may be realized as neural-network ("NN"), in particular a convolutional neuro-network ("CNN"). With continued reference to FIG. 11, this shows in more detail a CNN architecture as envisaged herein in embodiments.

The CNN is operable in two modes: "training mode/phase" and "deployment mode/phase". In training mode, an initial model of the CNN is trained based on a set of training data to produce a trained CNN model. In deployment mode, the pre-trained CNN model is fed with non-training, new data, to operate during normal use. The training mode may be a one-off operation or this is continued in repeated training phases to enhance performance. All that has been said so far in relation to the two modes is applicable to any kind of machine learning algorithms and is not restricted to CNNs or, for that matter, NNs.

The CNN comprises a set of interconnected nodes organized in layers. The CNN includes an output layer OL and an input layer IL. The input layer IL may be a matrix whose size (rows and columns) matches that of the training input image. The output layer OL may be a vector or matrix with size matching the size chosen for the image quality metrics, medical findings and treatment plans.

The CNN has preferably a deep learning architecture, that is, in between the OL and IL there is at least one, preferably two or more, hidden layers. Hidden layers may include one or more convolutional layers CL1, CL2 ("CL") and/or one or more pooling layers PL1, PL2 ("PL") and/or one or more fully connected layer FL1, FL2 ("FL"). CLs are not fully connected and/or connections from CL to a next layer may vary but are in generally fixed in FLs.

Nodes are associated with numbers, called "weights", which represent how the node responds to input from earlier nodes in a preceding layer.

The set of all weights defines a configuration of the CNN. In the learning phase, an initial configuration is adjusted based on the training data using a learning algorithm such as forward-backward ("FB")-propagation or other optimization schemes, or other gradient descent methods. Gradients are taken with respect of the parameters of the objective function.

The training mode is preferably supervised, that is, is based on annotated training data. For each pair, one item is the training input data and the other item is target training data known a priori to be correctly associated with its training input data item. This association defines the annotation and is preferably provided by a human expert. The training pair includes imagery as training input data, and associated with each training image, is target of label for any one or more of: image quality indication, indication of medical finding represented by that image, indication of a priority level, indication of workflow step(s) called for the given image.

As noted above, in the present disclosure, annotated training data includes pairs or training data items directly taken from the clinical workflow. Therefore, the training can be performed according to the standards of the institution. It can be determined by the institution which person is experienced enough for annotating the data. The above-proposed IT infrastructure may offer a method to integrate training of AI algorithms into the clinical workflow and to make the training user-specific. Optionally, the training can be performed according to the standards of the user group. The proposed IT infrastructure may offer a method to integrate training of AI algorithms into the clinical workflow and to make the training group-specific.

In training mode, preferably multiple such pairs are applied to the input layer to propagate through the CNN until an output emerges at OL. Initially, the output is in general different from the target. During the optimization, the initial configuration is readjusted so as to achieve a good match between input training data and their respective target for all pairs. The match is measured by way of a similarity measure, which can be formulated in terms of on objective function, or cost function. The aim is to adjust the parameters to incur low cost, that is, a good match.

More specifically, in the NN model, the input training data items are applied to the input layer (IL) and passed through a cascaded group(s) of convolutional layers CL1, CL2 and possibly one or more pooling layers PL1, PL2, and are finally passed to one or more fully connected layers. The convolutional module is responsible for feature based learning (e.g. identifying features in the patient characteristics and context data, etc.), while the fully connected layers are responsible for more abstract learning, for instance, the impact of the features on the treatment. The output layer OL includes the output data that represents the estimates for the respective targets.

The exact grouping and order of the layers as per FIG. 8 is but one exemplary embodiment, and other groupings and order of layers are also envisaged in different embodiments. Also, the number of layers of each type (that is, any one of CL, FL, PL) may differ from the arrangement shown in FIG. 8. The depth of the CNN may also differ from the one shown in FIG. 8. All that has been said above is of equal application to other NNs envisaged herein, such as fully connected classical perceptron type NN, deep or not, and recurrent NNs, or others.

The annotated (labelled) training data, as envisaged herein may need to be reformatted into structured form. As mentioned, the annotated training data may be arranged as vectors or matrices or tensor (arrays of dimension higher than 2). This reformatting may be done by a data preprocessor module (not shown), such as scripting program or filter that runs through patient records of the HIS of the current facility to pull up a set of patient characteristics.

The training data sets are applied to the initially configured CNN and is then processed according to a learning algorithm such as the FB-propagation algorithm as mentioned before. At the end of the training phase, the so pre-trained CNN may then be used in deployment phase to compute the decision support information for new data, that is, newly acquired copy images not present in the training data.

Alternatively, the data-driven model may be trained on the fly (i.e. during normal use of the data-driven model in the deployment phase) on the acquired image of the patient and the user annotation provided by the mobile annotation device 14. For example, each newly acquired image and the respective user annotation provided by the mobile annotation device 14 may be directly sent to the training module for updating the parameters of the data-driven model. In this way, the data-driven model is continuously trained, such that the data-driven model fits the needs and standards of a particular facility.

Some or all of the above-mentioned steps may be implemented in hardware, in software or in a combination thereof. Implementation in hardware may include a suitably programmed FPGA (field-programmable-gate-array) or a hard-wired IC chip. For good responsiveness and high throughput, multi-core processors such as GPU or TPU or similar may be used to implement the above described training and deployment of the machine learning model, in particular for NNs.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In FIGS. 1-8, the approach is described in relation with a data-driven model to analyze the acquired image of the patient to compute medical decision support information. It will be appreciated that the above-described approach may be adapted to any data-driven model.

For example, the data-driven model is a data-driven model for analyzing a camera image of the patient to compute the set of pre-image settings. Such a data-driven model correlates one or more features in the camera image with set of pre-image settings. In an example, the set of pre-image settings for an x-ray imaging system may include at least one of a tube voltage, a tube current, a grid, a collimation window, and a geometry parameter of a collimator. In a further example, the set of pre-image settings for a CT imaging system comprises at least one of a power supply level, a tube current, a dose modulation, a scan planning parameter, and a reconstruction parameter. The input of the data-driven model may include non-image patient data. The non-image patient data of the patient may comprise complementary information to the measurement image captured by the sensor arrangement. For example, the size of the lung is known to be correlated to the patient weight, age and gender and may be influenced by certain diseases like COPD. By additionally adding the non-patient image data obtained during the imaging procedure into the training set database, the data-driven model may be trained to better model the relation between the patient and the scan configuration, e.g. collimation settings, to be used in the exam preparation and/or in the imaging procedure. The data-driven model may comprise at least one of: an artificial neural network, and a classification tree using at least one of Haar-like, scale-invariant feature transform (SIFT), and speed up robust feature (SURF) image features.

For this exemplary data-driven model, the user interface 14c shown in FIG. 1 is configured to receive a user annotation in relation to the set of pre-image settings used by the medical imaging apparatus for acquiring the image of the patient. The training database 16 is configured to store the set of pre-image settings and the received user annotation. The training module 30 is configured to train the exemplary data-driven model with training data obtained from the at least one training database.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. An imaging system, comprising:
a medical imager configured to use a set of pre-image settings for acquiring an image of a patient in an imaging session;
a user interface configured to receive a user annotation in relation to the acquired image of the patient and the set of pre-image settings used by the medical imaging apparatus for acquiring the image of the patient to create annotated training data;
at least one training database configured to store the annotated training data that includes the acquired image of the patient, the received user annotation, and the set of pre-image settings; and
a training module configured to train at least one data-driven model with the annotated training data obtained from the at least one training database, wherein the at least one data-driven model is configured to:
analyze the acquired image of the patient to compute medical decision support information; and
analyze a camera image of the patient to compute the set of pre-image settings, wherein the camera image is generated from sensor data obtained from at least one sensor, which has a field of view that includes at least part of an area where the patient is positioned for the imaging session.

2. The imaging system according to claim 1, further comprising:
a mobile annotation device that comprises:
an input channel configured to receive the acquired image of the patient and/or the set of pre-image settings used by the medical imager for acquiring the image of the patient;
a display configured to display the acquired image of the patient and/or the set of pre-image settings used by the medical imager for acquiring the image of the patient;
the user interface configured to receive the user annotation in relation to the acquired image of the patient and/or the set of pre-image settings used by the medical imager for acquiring the image of the patient; and
an output channel configured to provide the acquired image of the patient, the received user annotation, and the set of pre-image settings to the at least one training database.

3. The imaging system according to claim 2, wherein the mobile annotation device is a handheld device including one or more of: a mobile phone, a laptop computing device, and a tablet computer.

4. The imaging system according to claim 1, wherein the training module is configured to repeatedly train the at least one data-driven model.

5. The imaging system according to claim 1, wherein the training module is configured to generate the user annotation on a random basis for starting training the at least one data-driven model.

6. The imaging system according to claim 1, wherein the at least one data-driven model is configured to provide a suggestion based on the computed medical decision support information for allowing a user to actively accept or reject the provided suggestion.

7. The imaging system according to claim 1, further comprising:
a first group of medical imagers and a second group of medical imagers, which is different from the first group of medical imager;
wherein the user interface is configured to receive:
a first user annotation in relation to the image of the patient acquired by a medical imager in the first group and/or a set of pre-image settings used by the medical imager in the first group; and
a second user annotation in relation to the image of the patient acquired by a medical imager in the second group and/or a set of pre-image settings used by the medical imager in the second group;
wherein the at least one training database comprises:
a first training database for storing the image of a patient acquired by the medical imager in the first group, the received user annotation, and the set of pre-image settings used by the medical imager in the first group; and
a second training database for storing the image of a patient acquired by the medical imager in the second group, the received user annotation, and the set of pre-image settings used by the medical imager in the second group;
wherein the training module is configured to train a first data-driven model with training data obtained from the first training database and to train a second data-driven model with training data obtained from the second training database.

8. The imaging system according to claim 7, wherein the first group of medical imagers and the second group of medical imagers are from different facilities and/or different user groups.

9. The imaging system according to claim 1, wherein the user annotation comprises one or more of:
an indication of image quality;
a clinical finding; and
an indication of a set of desired pre-image settings.

10. The imaging system according to claim 1, wherein the decision support information comprises one or more of:
a recommended workflow in relation to the patient;
an indication of an image quality in relation to the acquired image;
an indication on a medical finding; and
a priority information representing urgency of a medical finding.

11. A computer-implemented method of image processing, comprising:
acquiring, by a medical imager using a set of pre-image settings, an image of a patient in an imaging session;

receiving, via a user interface, a user annotation in relation to the acquired image of the patient and the set of pre-image settings used by the medical imager for acquiring the image of the patient to create annotated training data; storing, in at least one training database, the annotated training data that includes the acquired image of the patient, the received user annotation, and the set of pre-image settings; and training, by a training module, at least one data-driven model with the annotated training data obtained from the at least one training database, wherein the at least one data-driven model is configured to:

analyze the acquired image of the patient to compute medical decision support information; and analyze a camera image of the patient to compute the set of pre-image settings, wherein the camera image is generated from sensor data obtained from at least one sensor, which has a field of view that includes at least part of an area where the patient is positioned for the imaging session.

\* \* \* \* \*